United States Patent [19]
Egger et al.

[11] 3,936,486
[45] Feb. 3, 1976

[54] PROCESS FOR THE PRODUCTION OF MALONIC ACID DINITRILE
[75] Inventors: Alfons Egger; Erich Widmer; Adriano Faucci; Rolf Gregorin, all of Visp (Kanton Wallis), Switzerland
[73] Assignee: Lonza Ltd., Basel, Switzerland
[22] Filed: Oct. 18, 1974
[21] Appl. No.: 516,135

[30] Foreign Application Priority Data
Oct. 18, 1973 Switzerland.................. 14759/73

[52] U.S. Cl........................................ 260/465.8 R
[51] Int. Cl.² ............... C07C 120/00; C07C 121/22
[58] Field of Search .............. 260/465.8 A, 465.8 R

[56] References Cited
UNITED STATES PATENTS
| | | | |
|---|---|---|---|
| 3,541,133 | 11/1970 | Johnson et al. | 260/465.8 R |
| 3,655,721 | 4/1972 | Arni et al. | 260/465.8 R |
| 3,683,003 | 8/1972 | Aufdereggen et al. | 260/465.8 R |
| 3,729,499 | 4/1973 | Lussling et al. | 260/465.8 R |

Primary Examiner—Joseph P. Brust
Attorney, Agent, or Firm—Christen & Sabol

[57] ABSTRACT

The process for the production of malonic acid dinitrile which includes quickly preheating acetonitrile to a temperature between 110° and 700°C. Cyanogen chloride and the preheated acetonitrile, both in the gaseous state, are reacted at a temperature between 700° and 1200°C. Malonic acid dinitrile, in the gaseous state, results. The reaction product mixture of gaseous malonic acid dinitrile, gaseous cyanogen chloride, gaseous acetonitrile and HCl, a reaction by-product, is chilled with liquid reaction product mixture to a temperature between 40°C. and the boiling point of the reaction product mixture. A liquid reaction product results. Simultaneously with the chilling step, the exhaust gas resulting from the chilling of the reaction product mixture is distilled or refined to separate the cyanogen chloride and acetonitrile from the HCl component in the exhaust gas. The malonic acid dinitrile is isolated from the liquid reaction product mixture and purified.

30 Claims, 2 Drawing Figures

PROCESS FOR THE PRODUCTION OF MALONIC ACID DINITRILE

BACKGROUND OF THIS INVENTION

1. Field of this Invention

This invention relates to a process for the production of malonic acid dinitrile which involves reacting cyanogen chloride and acetonitrile in the gaseous phase at temperatures of 700° to 1200°C, chilling the reaction product mixture and isolating the malonic acid dinitrile from the reaction product mixture.

2. Prior Art

It is known to produce malonic acid dinitrile by reaction of cyanogen chloride and acetonitrile, both in the gaseous state, at a temperature above 600°C. (see U.S. Pat. No. 2,553,406).

German Application Nos. 1,768,154 and 1,911,174, which have been laid open to public inspection, teach producing malonic acid dinitrile from acetonitrile and cyanogen chloride at a medium reaction temperature below 800°C. and immediately chilling the gaseous reaction product, for example, with ice water, to a low temperature. If the reaction is carried out in the presence of water, then acid-binding substances are added.

German Pat. No. 1,281,424 teaches the reaction of acetonitrile and cyanogen chloride is described in the presence of certain catalysts at 800° to 950°C., or in the presence of chlorine or bromine, as a catalyst, at 700° to 950°C. In such process the reaction mixture is then chilled to a low temperature.

Swiss Patent No. 493,473 discloses the production of malonic acid dinitrile from acetonitrile and cyanogen chloride in the gaseous phase at a temperature of 740° to 780°C. At the same time a molar ratio of cyanogen chloride to acetonitrile of 1:1 to 1:5 is used. A tarry time of 1 to 15 seconds is used. The developing reaction product is cooled immediately, preferably by application of a cooling brine, to 20° to 50°C, and preferably to 25° to 30°C.

In all of the known processes, an attempt was made to chill (quench) the reaction product mixture as quickly as possible to as low a temperature as possible, because the assumption was made that the formation of secondary products could thus be avoided. As a result of such a rapid chilling to a low temperature, a part of the HCl formed during the reaction remained dissolved in the reaction mixture and resinifications developed nitrile compounds, which caused choking and incrustations both in the chilling part of the reactor as well as in the subsequent distillation. As a result of that the apparatus could only be used for a short time — which in practice leads to the fact that these processes were hardly usable technologically. If the chilling is carried out with the help of cooled acetonitrile (see German application No. 1,768,154), then there is the additional disadvantage that large quantities of HCl are still dissolved in the excess acetonitrile and the separation of the reaction mixture is made even more difficult. As has already been explained previously, this is exceedingly difficult because of the resinification and it can be carried out only on an uneconomical basis.

If alkalis are inserted simultaneously with the chilling for the purpose of neutralizing the hydrochloric acid formed, then considerable losses of acetonitrile as a result of hydrolysis cannot be avoided and the ammonium salts formed are an additional burden to the separating processes.

BROAD DESCRIPTION OF THIS INVENTION

An object of this invention is to provide an improvement in the production of malonic acid dinitrile which increases the space-time-yield (capacity) of the reaction equipment, which decreases the loss of acetonitrile, which decreases the yield of polymeric by-products that lead to resinification, and which technologically simplify the processing of the reaction product mixture.

Other objects and advantages of this invention are set out in this application or are obvious to one ordinarily skilled in the art.

Such objects and advantages are achieved by this invention.

This invention broadly involves a process which includes preheating acetonitrile to a temperature of 110° to 700°C., reacting the preheated acetonitrile with cyanogen chloride, chilling the gaseous reaction product mixture with liquid reaction product mixture to a temperature between 40°C. and the boiling temperature of the reaction product while simultaneously stripping (refining) the exhaust gases and isolating and purifying the resultant malonic acid dinitrile.

This invention involves a process for the production of malonic acid dinitrile. The process involves quickly preheating acetonitrile to a temperature between 110° and 700°C. Cyanogen chloride and the preheated acetonitrile, both in the gaseous state, are reacted at a temperature between 700° and 1200°C. Malonic acid dinitrile, in the gaseous state, results. The reaction product of gaseous malonic acid dinitrile, gaseous cyanogen chloride, gaseous acetonitrile and gaseous HCl, a reaction by product, are chilled with liquid reaction product mixture to a temperature between 40°C. and the boiling point of the reaction product mixture. A liquid reaction product results. Simultaneously with the chilling step, the exhaust gas from the chilling of the reaction product mixture is distilled or refined to separate the cyanogen chloride and/or acetonitrile from the HCl component in the exhaust gas. The malonic acid dinitrile from the liquid reaction product mixture is isolated and purified.

Preferably the acetonitrile is quickly preheated to a temperature between 200° and 700°C, and most preferably to a temperature between 600° and 650°C. Preferably the acetonitrile is preheated by passing the acetonitrile through a preheater at a velocity between 20 and 100 m/sec., and most preferably at a velocity between 50 and 70 m/sec. Preferably the molar ratio of the acetonitrile and the cyanogen chloride in the reactor is between 1:1 and 6:1.

Preferably the reaction product mixture is chilled to a temperature between 55° and 78°C., and most preferably to a temperature between 60° and 70°C. Preferably a portion of the liquid reaction product mixture obtained from the chilling step is used as the liquid reaction product mixture used in the chilling step to achieve the chilling of the reaction product mixture. Preferably part or all of the acetonitrile recovered from said liquid reaction product is recycled to the acetonitrile preheating step. Preferably part or all of the acetonitrile recovered from said exhaust gas is recycled to the acetonitrile preheating step. Preferably the malonic acid dinitrile is isolated from the liquid reaction product mixture by means of distillation.

The chilling or quenching step should be carried out as rapidly as possible. The chilling time is in the order of magnitude of the known chilling times.

This invention and many of its advantages resides a great deal in its novel combination of preheating-chilling. This becomes clear from the space-time-yield and from the shelf lives. ("Shelf live", as used herein, is the time after which the apparatus must be cleaned.)

DETAILED DESCRIPTION OF THIS INVENTION

The preheating of the acetonitrile to a temperature of 110° to 700°C., preferably 600° to 650°C., considerably increases the space-time-yield (capacity) of the reactor. Applicants were afraid that as a result of preheating the acetonitrile to the above-mentioned temperature a decomposition of the acetonitrile would occur, but surprisingly that was not the case. The preheating of the gaseous acetonitrile is accomplished as quickly as possible and without overheating at the heating surface. This can be accomplished by passing the acetonitrile vapor at a high speed through a preheater, preferably a preheating pipe. A velocity of 20 to 100 m/sec. is used effectively, and preferably the velocity is 50 to 70 m/sec.

The preheated acetonitrile and the cyanogen chloride are reacted in the reactor effectively at a molar ratio between 1:1 and 6:1, at a tarry time of fractions of a second (e.g., 0.3 second) up to a few seconds (e.g., 10 seconds) and at a temperature between 700° and 1200°C.

Subsequently the gaseous reaction product mixture is chilled by means of liquid (condensable) reaction product mixture at a temperature of more than 40°C., up to almost the boiling temperature of the reaction product mixture. The boiling temperature of the reaction product mixture in the case of standard pressure lies approximately between 75° and 78°C., depending on the composition of the reaction product mixture. If one operates at above atmospheric pressure, then the boiling temperature increases and thus also does the chilling temperature. Effectively, chilling is accomplished at standard pressure and at a temperature of 55° to 78°C, preferably 60° to 70°C.

As used herein the term reaction product mixture means a mixture of unreacted acetonitrile and cyanogen chloride, malonic acid dinitrile and HCl. The liquid reaction product mixture will not contain all or most of the HCl (byproduct).

A part of the liquid (condensed) reaction product mixture is brought to the desired temperature by circulation through heat exchanges and is used as the chilling liquid. The remaining part of the liquid reaction product mixture is drawn off from the chilling part of the apparatus. The acetonitrile which has not been converted is separated and the latter is fed to the reaction in circulation; that is to say after preheating, it is again reacted.

The malonic acid dinitrile is isolated from the liquid reaction product mixture using any suitable isolation method, but distillation is preferred and reduced-pressure distillation is most preferred.

The crude malonic acid dinitrile obtained during the distillation is processed or purified using conventional and known methods into a pure product.

During the chilling (quenching) the exhaust gas which consists mainly of gaseous HCl is refined (separated) from the reaction product mixture. With the help of a proper reflux system, the condensable portions which had been carried along, mostly acetonitrile, are returned (after preheating) to the reaction site. The HCl obtained in the case of the reaction of cyanogen chloride and acetonitrile is refined (separated) in this manner without any particular problems. As a result of that the acetonitrile, which is recovered during the distillation (isolation step) of the liquid reaction product mixture, also contains essentially no HCl or only such slight traces of HCl that the acetonitrile can be recycled without difficulty to the preheating system. As a result of this, no corrosion problems occur.

Figure 1:
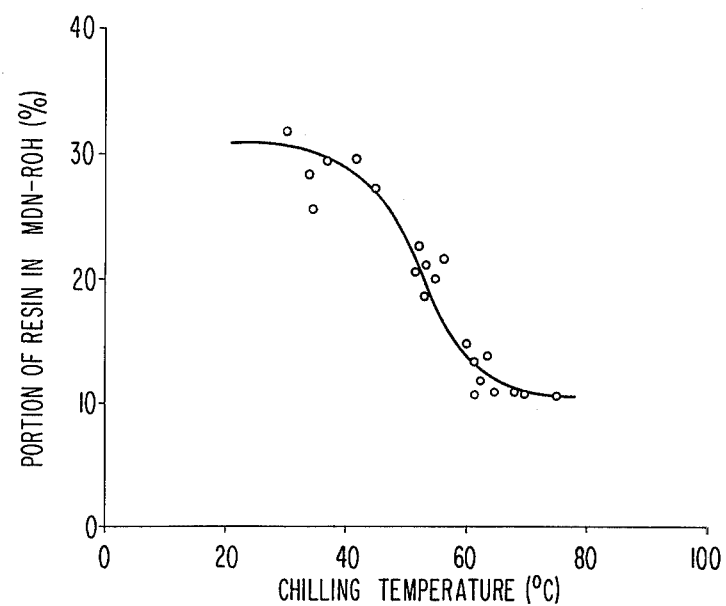
FIG. 1 is a graph of resin content vs. chilling temperature.
Figure 2:
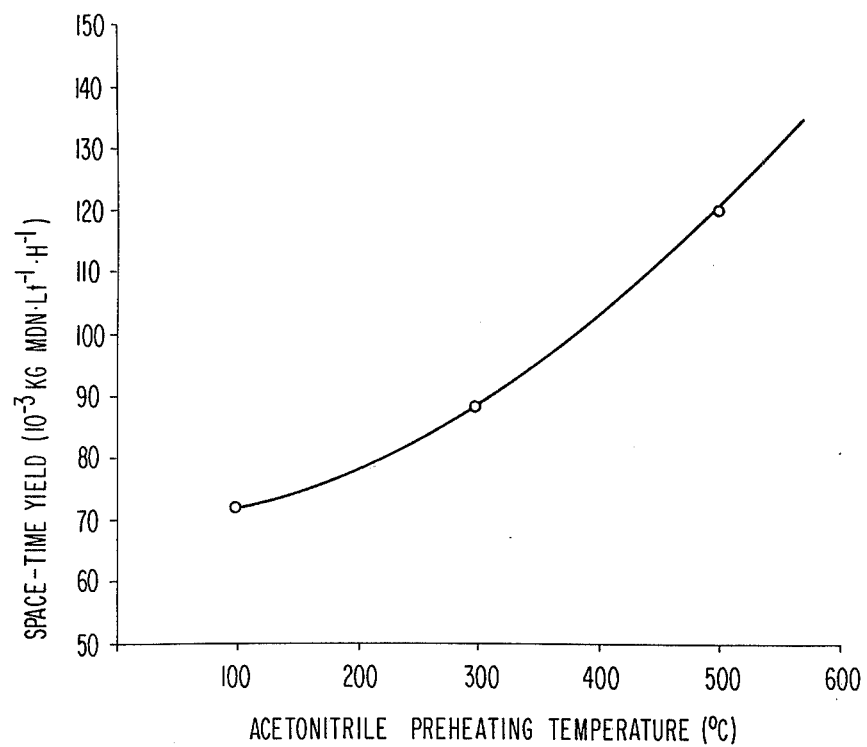
FIG. 2 is a graph of the preheating temperature of acetonitrile vs. the space-time-yield for the subject reaction.

FIG. 1 shows the relationship between the chilling temperature and the formation of resin and FIG. 2 shows the relationship between the preheating temperature and space-time-yield (both for a particular reactor geometry and dimensions). From this it is quite clear, that the improvements of the known process achieved by this invention makes the production of malonic nitrile from acetonitrile and cyanogen chloride technically feasible.

EXAMPLE 1

INFLUENCE OF THE CHILLING TEMPERATURE: RESIN PORTION IN THE MDN - ROH

After condensation of the reaction temperature by chilling, the excess acetonitrile was distilled off under reduced pressure. The bubble product, termed MDN - ROH, had a resin portion which is directly dependent upon the chilling temperature — this is shown in FIG. 1. (MDN = malonic acid dinitrile; ROH is equated to the resin portion) SHELF LIFE OF THE CHILLING AND OF THE RECTIFICATION Example:

| Quenching temperature | shelf life | |
|---|---|---|
| | chilling | rectification |
| 20° to 30°C | 2 to 3 days | 5 days |
| 60 to 70°C. | 30 days | 30 days |

| Acetonitrile-preheater-temperature | Space-time yield | |
|---|---|---|
| 100°C. | 0.0708 kg | MDN·lt$^{-1}$·h$^{-1}$ |
| 300°C | 0.089 | MDN |
| 400°C | 0.1165 | MDN |
| 500°C | 0.126 | MDN |

The following examples of the process according to this invention and examples of the known processes, by means of comparison, show the unexpected and sizable progress which is achieved by the measures of this invention.

EXAMPLE 2

(comparative example)

Cyanogen chloride and acetonitrile were reacted, forming malonic acid dinitrile, in a reactor system at a molar ratio of 1:5.7, at a mean temperature of 815°C. and at a tarry time of 2 seconds. The evaporated acetonitrile was fed to the reactor at a temperature of 100°C. The space-time-yield amounted to 0.0708 kg . lt$^{-1}$ . h$^{-1}$.

EXAMPLE 3

In the same reactor system and under otherwise identical conditions as in Example 2, but with a preheating of the acetonitrile to 500°C. a space-time-yield of 0.126 kg . $lt^{-1}$ . $h^{-1}$ was achieved.

EXAMPLE 4

(comparative example)

With subsequent separation of excess acetonitrile, cyanogen chloride and acetonitrile were converted to malonic acid dinitrile in a reactor system at a molar ratio of 1:5.7, at a mean temperature of 815°C. and at a tarry time of 2 seconds. The chilling of the reaction product mixture took place at 30° using liquid (condensed) reaction product mixture. The portion of resin in the crude malonic acid dinitrile (after separation of the acetonitrile) amounted to 32 percent by weight. At two day intervals, the chilling equipment was completely resinified ("clogged-up") and had to be cleaned out after stopping the reactor assembly. The distillation (refining) column for the acetonitrile, although it was equipped with installations which were not very subject to displacement, had to be cleaned out after five day intervals.

EXAMPLE 5

In the same reactor system as described in Example 4 and under otherwise identical conditions, the chilling was accomplished at temperature of 70° by returning the liquid (condensed) reaction product mixture. The portion of the resin in the crude malonic acid dinitrile amounted to only 10 percent by weight. After 30 days, the chilling equipment was still so little resinified ("clogged-up") that no cleaning was needed; and the acetonitrile distillation (refining) column could be operated for 30 days without cleaning.

Examples 3 and 5 represent this invention. Example 3 shows increased space-time-yield as compared to Example 2. Example 5 shows decreased resin formation ascompared to Example 4.

As used in this application, parts, percentages, ratios and proportions are on a weight basis unless otherwise stated or obvious to one ordinarily skilled in the art.

What is claimed is:

1. The process for the production of malonic acid dinitrile which comprises:
   a. quickly preheating acetonitrile to a temperature between 110° and 700°C. by passing said acetonitrile through a preheater at a velocity between 20 and 100 m/sec.;
   b. reacting a reaction admixture of cyanogen chloride and said acetonitrile, both in the gaseous state, the molar ratio of said acetonitrile and said cyanogen chloride is between 1:1 and 6:1, at a temperature between 700° and 1200°C., malonic acid dinitrile, in the gaseous state, resulting;
   c. chilling the reaction product mixture of step (b) which is comprised of said gaseous malonic acid dinitrile, said gaseous cyanogen chloride, said gaseous acetonitrile and HCl, a reaction byproduct, with liquid mixture, which is comprised of malonic acid dinitrile, cyanogen chloride, acetonitrile and HCl, to a temperature between 40°C. and the boiling point of said reaction product mixture, a liquid reaction product resulting;
   d. simultaneously with step (c), refining the exhaust gas from said chilling of said reaction product mixture of step (c) whereby the cyanogen chloride and acetonitrile is separated from the HCl in the exhaust gas; and
   e. isolating said malonic acid dinitrile from said liquid reaction product mixture and purifying said malonic acid dinitrile.

2. The process of claims 1 wherein said acetonitrile is quickly preheated to a temperature between 200° and 700°C.

3. The process of claim 2 wherein said acetonitrile is quickly preheated to a temperature between 600° and 650°C.

4. The process of claim 3 wherein said acetonitrile is preheated by passing said acetonitrile through a preheater at a velocity between 50 and 70 m/sec.

5. The process of claim 3 wherein said refining of step (d) involves distilling said exhaust gas whereby said cyanogen chloride and said acetonitrile are separated from said HCl in said exhaust gas.

6. The process of claim 3 wherein said chilling step is achieved at standard pressure.

7. The process of claim 3 wherein said reaction product mixture is chilled in step (c) to a temperature between 55° and 78°C.

8. The process of claim 3 wherein said reaction product mixture is chilled in step (c) to a temperature between 60° and 70°C.

9. The process of claim 2 wherein part of all of the acetonitrile recovered from said liquid reaction product is recycled to step (a).

10. The process of claim 2 wherein part or all of the acetonitrile recovered from said exhaust gas is recycled to step (a).

11. The process of claim 2 wherein part of said liquid reaction product mixture obtained by step (d) is used as the liquid reaction product mixture used in step (d) to achieve said chilling of said reaction product mixture.

12. The process of claim 2 wherein said malonic acid dinitrile is isolated from said liquid reaction product mixture by means of distillation.

13. The process of claim 3 wherein said distillation is reduced-pressure distillation.

14. The process of claim 2 wherein said reaction admixture has a tarry time of 0.3 to 10 seconds.

15. The process of claim 1 wherein said acetonitrile is quickly preheated to a temperature between 300° and 700°C.

16. The process for the production of malonic acid dinitrile which consists of:
   a. quickly preheating acetonitrile to a temperature between 110° and 700°C. by passing said acetonitrile through a preheater at a velocity between 20 and 100 m/sec.;
   b. reacting a reaction admixture of cyanogen chloride and said acetonitrile, both in the gaseous state, the molar ratio of said acetonitrile and said cyanogen chloride is between 1:1 and 6:1,
   c. chilling the reaction product mixture of step (b) which is comprised of said gaseous malonic acid dinitrile, said gaseous cyanogen chloride, said gaseous acetonitrile and HCl, a reaction byproduct, with liquid mixture, which is comprised of malonic acid dinitrile, cyanogen chloride, acetonitrile and HCl, to a temperature between 40°C. and the boiling point of said reaction product mixture, a liquid reaction product resulting;
d. simultaenously with step (c), refining the exhaust gas from said chilling of said reaction product mixture of step (c) whereby the cyanogen chloride and acetonitrile is separated from the HCl in the exhaust gas; and
e. isolating said malonic acid dinitrile from said liquid reaction product mixture and purifying said malonic acid dinitrile.

17. The process of claim 16 wherein said acetonitrile is quickly preheated to a temperature between 200° and 700°C.

18. The process of claim 17 wherein said acetonitrile is quickly preheated to a temperature between 600° and 650°C.

19. The process of claim 18 wherein said acetonitrile is preheated by passing said acetonitrile through a preheater at a velocity between 50 and 70 m/sec.

20. The process of claim 18 wherein said refining of step (d) involves distilling said exhaust gas whereby said cyanogen chloride and said acetonitrile are separated from said HCl in said exhaust.

21. The process of claim 18 wherein said chilling step is achieved at standard pressure.

22. The process of claim 18 wherein said reaction product mixture is chilled in step (c) to a temperature between 55° and 78°C.

23. The process of claim 18 wherein said reaction product mixture is chilled in step (c) to a temperature between 60° and 70°C.

24. The process of claim 17 wherein part or all of the acetonitrile recovered from said liquid reaction product is recycled to step (a).

25. The process of claim 17 wherein part or all of the acetonitrile recovered from said exhaust gas is recycled to step (a).

26. The process of claim 17 wherein part of said liquid reaction product mixture obtained by step (d) is used as the liquid reaction product mixture used in step (d) to achieve said chilling of said reaction product mixture.

27. The process of claim 17 wherein said malonic acid dinitrile is isolated from said liquid reaction product mixture by means of distillation.

28. The process of claim 17 wherein said distillation is reduced-pressure distillation.

29. The process of claim 17 wherein said reaction admixture has a tarry time of 0.3 to 10 seconds.

30. The process of claim 17 wherein said acetonitrile is preheated to a temperature between 300° and 700°C.

* * * * *